United States Patent [19]
Warren

[11] Patent Number: 5,400,805
[45] Date of Patent: Mar. 28, 1995

[54] SURGICAL FASTENER

[75] Inventor: Russell Warren, Greenwich, Conn.

[73] Assignee: American Cyanamid Company, Wayne, N.J.

[21] Appl. No.: 126,956

[22] Filed: Sep. 24, 1993

Related U.S. Application Data

[60] Division of Ser. No. 490,529, Mar. 5, 1990, Pat. No. 5,261,914, which is a continuation of Ser. No. 92,121, Sep. 2, 1987, abandoned.

[51] Int. Cl.$^6$ .............................................. A61B 17/04
[52] U.S. Cl. ...................................... 128/898; 606/72; 606/104
[58] Field of Search ........................ 606/72, 73, 76, 77, 606/103, 104, 232; 128/898

[56] References Cited

U.S. PATENT DOCUMENTS

| | | | |
|---|---|---|---|
| 4,924,865 | 5/1990 | Bays et al. | 606/77 |
| 4,976,715 | 12/1990 | Bays et al. | 606/77 |
| 5,084,050 | 1/1992 | Draenert | 606/77 |
| 5,129,906 | 7/1992 | Ross et al. | 606/77 |
| 5,211,647 | 5/1993 | SChmieding | 606/73 |
| 5,246,441 | 9/1993 | Ross et al. | 606/77 |
| 5,258,016 | 11/1993 | DiPoto et al. | 606/104 |

*Primary Examiner*—Stephen C. Pellegrino
*Assistant Examiner*—Gary Jackson
*Attorney, Agent, or Firm*—D. E. Denninger

[57] ABSTRACT

A novel surgical fastener is disclosed for attaching soft tissues (e.g. ligaments, tendons and the like) to bone and bone-like structures. The surgical fastener comprises a shank and an enlarged head disposed on one end of the shank. A central bore passes completely through the fastener along its longitudinal axis, and a plurality of diametrically projecting ribs are disposed along the length of the shank. The foregoing fastener is used to attach soft tissues (e.g. ligaments, tendons and the like) to bone and bone-like structures in the following manner. First, the soft tissue is placed against the bone and then a thin guide wire is passed through the soft tissue and into the bone. A cannulated drill is then loaded coaxially onto the guide wire and is moved down the guide wire and worked on the guide wire so as to form a hole through the soft tissue and into the bone. Next, the cannulated drill is withdrawn from the guide wire and the aforementioned surgical fastener is loaded coaxially onto the guide wire. Then a hollow driver is loaded coaxially onto the guide wire and is used to successively strike the head of the fastener so as to drive the shank of the fastener through the soft tissue and into the bone, with the head of the fastener engaging the soft tissue and captivating it against the bone. Thereafter, the hollow driver is withdrawn from the guide wire, and then the guide wire is removed from the soft tissue and the bone, leaving the soft tissue securely attached to the bone by the surgical fastener.

22 Claims, 3 Drawing Sheets

SURGICAL FASTENER

This is a divisional of application Ser. No. 07/490,529, filed on Mar. 5, 1990, now U.S. Pat. No. 5,261,914, which is a continuation of Ser. No. 07/092,121, filed on Sep. 2, 1987, now abandoned.

FIELD OF THE INVENTION

This invention relates to surgical devices in general, and more particularly to surgical fasteners of the sort adapted to attach soft tissues (e.g. ligaments, tendons and the like) to bone and bone-like structures.

BACKGROUND OF THE INVENTION

Numerous surgical fasteners have been developed for use in joining together two or more body parts and/or prosthetic devices. See, for example, U.S. Pat. Nos. 3,716,058 (Tanner, Jr.), 4,060,089 (Noiles), 4,263,903 (Griggs), 4,454,875 (Pratt et al.), 4,548,202 (Duncan), 4,570,623 (Ellison et al.), 4,580,563 (Gross), 4,590,928 (Hunt et al.), and 4,635,637 (Schreiber), and the references cited therein, and PCT Publication No. WO 85/03857 (Schreiber).

Still other fasteners have been developed for use in joining together two or more parts. See, for example, U.S. Pat. Nos. 2,523,239 (Tinnerman), 2,853,913 (Rapata), 2,927,497 (Rapata), 3,494,244 (Wayland), 3,810,279 (Swick et al.), 4,395,174 (Freeman), 4,396,329 (Wollar), 4,402,641 (Arff), 4,427,328 (Kojima), and 4,551,189 (Peterson), and the references cited therein, and UK Patent Specification No. 520169 (Universal Rubber Paviors Limited) and Canadian Patent No. 1015989 (Russo).

OBJECTS OF THE INVENTION

One of objects of the present invention is to provide a novel surgical fastener of the sort adapted to attach soft tissues (e.g. ligaments, tendons and the like) to bone and bone-like structures.

Another object of the present invention is to provide a novel surgical fastener of the sort adapted to attach soft tissues (e.g. ligaments, tendons and the like) to bone and bone-like structures, wherein the fastener is designed to minimize bone necrosis.

Still another object of the present invention is to provide a novel surgical fastener of the sort adapted to attach soft tissues (e.g. ligaments, tendons and the like) to bone and bone-like structures, wherein the fastener is designed to be used arthroscopically.

And another object of the present invention is to provide novel means for deploying the aforementioned surgical fastener in a remote, e.g. arthroscopic, location.

Yet another object of the present invention is to provide a complete system for attaching soft tissues (e.g. ligaments, tendons and the like) to bone and bone-like structures.

And still another object of the present invention is to provide a novel method for attaching soft tissues (e.g. ligaments, tendons and the like) to bone and bone-like structures.

SUMMARY OF THE INVENTION

These and other objects of the present invention are achieved through the use of a novel surgical fastener which comprises a shank and an enlarged head disposed on one end of the shank. A central bore passes completely through the fastener along its longitudinal axis, and a plurality of radially projecting ribs are disposed along the length of the shank.

The foregoing fastener is used to attach soft tissues (e.g. ligaments, tendons and the like) to bone and bone-like structures in the following manner. First, the soft tissue is placed against the bone and then a thin guide wire is passed through the soft tissue and into the bone. A cannulated drill is then loaded coaxially onto the guide wire and is moved down the guide wire and worked on the guide wire so as to form a hole through the soft tissue and into the bone. Next, the cannulated drill is withdrawn from the guide wire and the aforementioned surgical fastener is loaded coaxially onto the guide wire. Then a hollow driver is loaded coaxially onto the guide wire and is used to successively strike the head of the fastener so as to drive the shank of the fastener through the soft tissue and into the bone, with the head of the fastener engaging the soft tissue and captivating it against the bone. Thereafter, the hollow driver is withdrawn from the guide wire, and then the guide wire is removed from the soft tissue and the bone, leaving the soft tissue securely attached to the bone by the surgical fastener.

BRIEF DESCRIPTION OF THE DRAWINGS

These and other objects and features of the present invention will be more fully disclosed or rendered obvious in the following detailed description of the invention, which is to be considered together with the accompanying drawings wherein like numbers refer to like parts and further wherein.

DETAILED DESCRIPTION OF THE INVENTION

Figure 1:
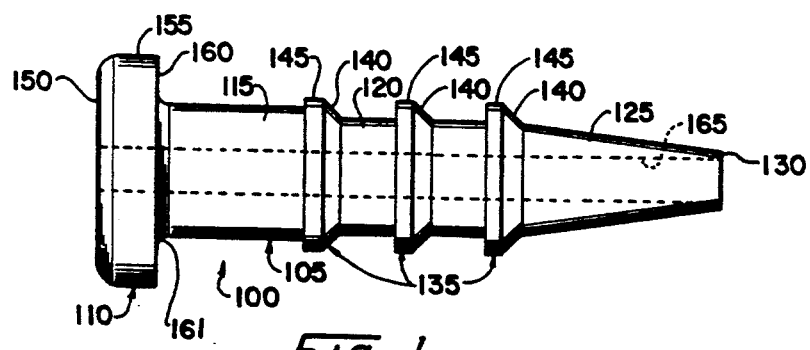
FIG. 1 is a side elevation of a surgical fastener made in accordance with the present invention.
Figure 2:
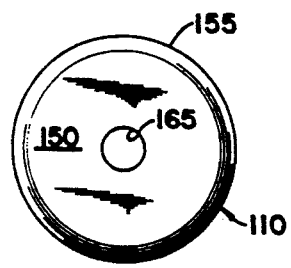
FIG. 2 is a top view of the same surgical fastener, taken along line 2—2 of FIG. 1.
Figure 3:
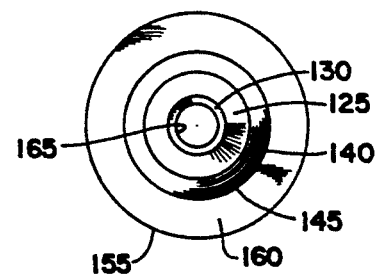
FIG. 3 is a bottom view of the same surgical fastener, taken along line 3—3 of FIG. 1.

Looking first at FIGS. 1–3, there is shown a surgical fastener 100 made in accordance with the present invention. Fastener 100 comprises a shank 105 and a head 110 which are preferably formed integral with one another. Shank 105 comprises a first portion 115 which has an outer diameter of approximately 0.138 inches, a second portion 120 which has an outer diameter of approximately 0.118 inches, and a third portion 125 which has an outer diameter of approximately 0.118 inches adjacent second portion 120 and which narrows (at approximately an 8 degree–14 degree taper) to a diameter of approximately 0.063 inches immediately adjacent the fastener's front tip surface 130.

Shank 105 has three radially projecting ribs 135 disposed along its length. One of the ribs 135 is disposed at the intersection of first portion 115 and second portion 120, one of the ribs 135 is disposed at the intersection of second portion 120 and third portion 125, and one of the ribs is disposed intermediate the length of second portion 120. Ribs 135 each comprise a leading surface 140 set at an approximately 45 degree angle to the longitudinal axis of fastener 100, and a peripheral surface 145 which extends approximately 0.020 inches along the longitudinal axis of fastener 100 and which has an outer diameter of approximately 0.157 inches.

Head 110 has an outer diameter of approximately 0.256 inches and terminates in a top end surface 150, a cylindrical side surface 155 and a lower surface 160. Head 110 has a thickness of approximately 0.069 inches, when measured from its top end surface 150 to its lower surface 160.

Surgical fastener 100 has an overall length of approximately 0.710 inches, when measured from its front tip surface 130 to its top (i.e., trailing) end surface 150.

A bore 165 having an internal diameter of approximately 0.048 inches passes completely through the fastener along its longitudinal axis, i.e., it extends from the fastener's front tip surface 130 to its top (i.e., trailing) end surface 150.

Looking next at FIGS. 4–8, the aforementioned surgical fastener 100 is intended to be used to attach a soft tissue (e.g. a ligament, tendon or the like) 200 to a bone (or another bone-like structure) 300.

For the sake of convenience, soft tissue 200 will hereinafter be described as a ligament 200; however, it is to be understood that member 200 might also constitute a tendon or some other type of soft tissue which is to be attached to a bone (or another bone-like structure) 300.

Figure 4:
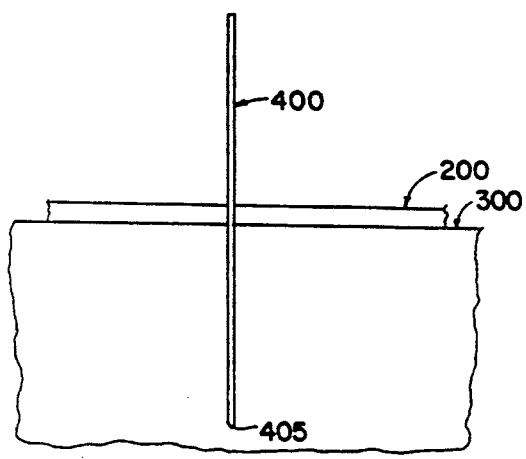
FIG. 4 is a partial side elevation showing a soft tissue (e.g. a ligament, tendon or the like) placed against a bone, with a guide wire having been inserted through the soft tissue and into the bone.

Looking specifically now at FIG. 4, ligament 200 is first positioned against the bone 300 which it is to be attached to. Next, a long thin guide wire 400 is passed through ligament 200 and into bone 300. Guide wire 400 has a diameter of approximately 0.035 inches and its leading tip 405 preferably penetrates bone 300 to a depth of at least 0.75 inches. It is to be appreciated that the guide wire's leading tip 405 is substantially pointed so that it can more easily penetrate through ligament 200 and into bone 300. Guide wire 400 may be emplaced simply by pushing it through the ligament and into the bone, or it may be mounted in a drilling device (not shown) to facilitate entry. In the event that the guide wire 400 is intended to be simply pushed through ligament 200 and into bone 300, a supporting cannula of the sort well known in the art (not shown) may be concentrically mounted around at least a portion of the guide wire during insertion so as to help maintain the linear shape of the guide wire during penetration. If such a supporting cannula is used, it is removed from around the guide wire as soon as the guide wire has been properly positioned in the manner shown in FIG. 4. Alternatively, in the event that guide wire 400 is intended to be drilled through ligament 200 and into bone 300, the guide wire's leading tip 405 may also include a helical drilling thread (not shown) to facilitate penetration. If a drilling device is used to deploy guide wire 400, the drilling device is detached from the guide wire as soon as the guide wire has been properly positioned in the manner shown in FIG. 4.

Figure 5:
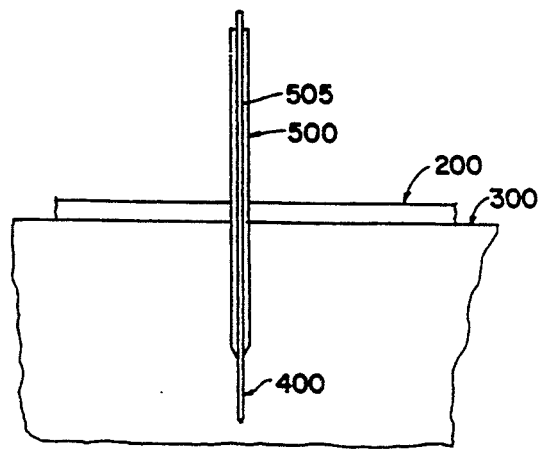
FIG. 5 is a view like that of FIG. 4, except that a cannulated drill has been loaded coaxially onto the guide wire and used to drill through the soft tissue and into the bone.

Looking next at FIG. 5, a cannulated drill 500 having an axial bore 505 is then concentrically mounted onto the free top end of guide wire 400 and is moved downward along the guide wire until the drill's leading tip contacts the upper surface of ligament 200. Then, using guide wire 400 as a drilling guide, cannulated drill 500 is drilled through ligament 200 and into bone 300. Cannulated drill 505 is sized so as to form a hole approximately 0.134 inches in diameter in ligament 200 and bone 300. Cannulated drill 500 cuts into bone 300 to a depth of approximately 0.75 inches, whereupon it is withdrawn from ligament 200 and bone 300 and then removed from the guide wire. It is to be appreciated that the entire time the foregoing is being accomplished, guide wire 400 is left in place in bone 300.

Figure 6:
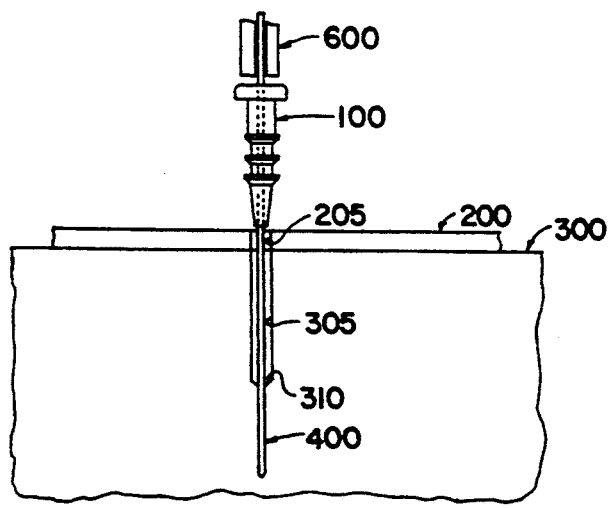
FIG. 6 is a view like that of FIG. 5, except that the cannulated drill has been removed from the guide wire and a surgical fastener of the type shown in FIG. 1 has been loaded coaxially onto the guide wire, and a hollow driver has been loaded coaxially onto the guide wire.

It is also to be appreciated that when cannulated drill 500 is removed from guide wire 400, a hole will be left in ligament 200 and bone 300, with guide wire 400 being disposed axially within the hole. As seen in FIG. 6, the portion of the hole extending through ligament 200 (indicated generally at 205) may tend to close somewhat upon the withdrawal of cannulated drill 500 due to the somewhat resilient nature of ligament 200, whereas the portion of the hole extending into bone 300 (indicated generally at 305) may not. The hole portion 305 will tend to terminate in a bone shoulder 310 at the base of the hole.

Looking now at FIG. 6, the surgical fastener 100 is then loaded concentrically onto guide wire 400, with the fastener's front tip surface 130 leading, so that the guide wire passes through the fastener's central bore 165. Depending on the tightness of the fit between fastener 100 and guide wire 400, as well as the presence of any intervening obstacles, fastener 100 may then slide down guide wire 400 under the influence of gravity until the fastener contacts ligament 200, or it may simply sit at the top end of guide wire 400, waiting to be urged down the guide wire. In this respect, it is to be appreciated that even if fastener 100 should migrate down guide wire 400 on its own, inasmuch as the hole 205, 305 formed in ligament 200 and bone 300 has a diameter of approximately 0.134 inches, and inasmuch as ligament 200 may also tend to close somewhat about the hole portion 205 as noted above, and also inasmuch as the ribs 135 of fastener 100 have an outer diameter of approximately 0.157 inches, the fastener will in any case tend to engage and be stopped by the ligament.

Still looking at FIG. 6, a hollow driver 600 is then coaxially fitted onto the free top end of guide wire 400. Hollow driver 600 has an internal bore diameter of approximately 0.055 inches and an external diameter of approximately 0.25 inches, whereby hollow driver 600 can move easily up and down guide wire 400 to contact the head of fastener 100.

Figure 7:
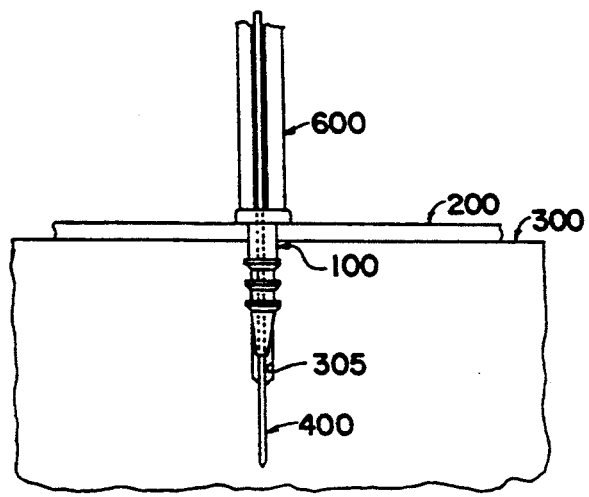
FIG. 7 is a view like that of FIG. 6, except that the fastener has been fully driven through the soft tissue and into the bone by the hollow driver so as to securely fasten the soft tissue to the bone.

Looking next at FIG. 7, hollow driver 600 is then used to first move fastener 100 down the guide wire to engage ligament 200 if the fastener is not yet in engagement with the ligament, and then to repeatedly strike fastener 100 on its upper surface 150, whereby the fastener's shank can be driven through ligament 200 and into bone 300 so that the shank locks itself into bone 300 while the head of the fastener captivates the ligament against the bone. It is to be appreciated that ribs 135 are sized and formed so that they strongly engage, and form a good grip with, the walls of bone 300 defining bore portion 305.

Figure 8:
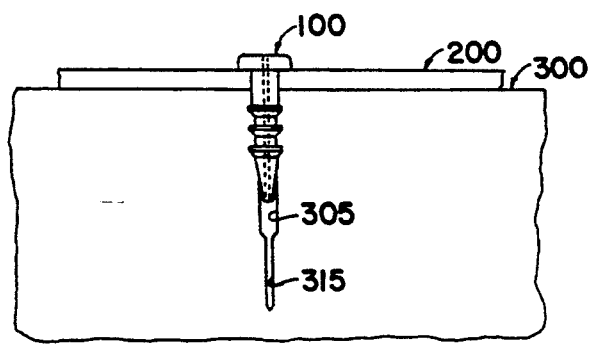
FIG. 8 is a view like that of FIG. 7, except that the hollow driver and the guide wire have been removed.

Finally, once the fastener has been completely driven into bone 300 so that the head of the fastener securely captivates the ligament against the bone, hollow driver 600 is withdrawn from it coaxial position on guide wire 400, and guide wire 400 is then withdrawn from fastener 100, ligament 200 and bone 300, leaving fastener 100, ligament 200 and bone 300 securely disposed in the positions shown in FIG. 8. It is to be appreciated that upon the removal of guide wire 400 from bone 300, an additional bore section 315 (corresponding to the location of guide wire 400 prior to its removal) may remain in bone 300 below bore section 305. It is also to be appreciated that upon the removal of guide wire 400 from bone 300, the fastener's central bore 165 may then be sealed by ways well known in the art (e.g. by filling with bone wax) so as to seal off the interior of bone 300 from the region outside the bone. In some circumstances it may be desired to have fastener 100 remain permanently in the body, without any substantial degradation over time; in this event, fastener 100 may be formed out of materials such as polypropylene, Hytrel (R) copolyester, or homopolymer polyesters, e.g. polyethylene terephthalate or polybutylene terephthalate, or nylon, or polyethylene, or polycarbonate, or acrylonitrile butadiene styrene block copolymers.

In other circumstances it may be desired to have fastener 100 remain intact in the body only temporarily, and to have it thereafter degrade and be naturally absorbed into the body after the passage of some time interval; in this event, fastener 100 may be formed out of materials such as homo and copolymers of glycolide and trimethylene carbonate, homo and copolymers of lactide and glycolide, or a blend of these homopolymers and copolymers. Such fasteners may also be coated with longer lasting materials, e.g. caprolactone and glycolide homo and copolymers, or glycolide and lactide homo and copolymers. Of course, the exact composition of such absorbable fasteners will vary according to the absorption characteristics desired. Such compositions are well known to persons skilled in the art.

The fasteners may also be made out of composites of the foregoing nonabsorbable and absorbable materials and bone growth promoters, e.g. hydroxyapatite, calcium phosphate, etc., or other ceramics.

The fasteners may also be coated with functional agents such as antibiotics, anticancer drugs, etc. to facilitate delivery of the agents to the implant site.

If possible, fastener 100 is preferably formed out of a slightly resilient material, whereby the fastener's ribs 135 may deform slightly upon engagement with ligament 200 and especially bone 300 and thereafter "spring back" to form a good grip with the walls of bone 300 defining bore portion 305. Also, if possible, fastener 100 is formed out of a material known to minimize bone necrosis.

It should be noted that certain features of fastener 100 facilitate its deployment and function. For example, the narrowing character of the fastener's shank portion 125 provides a somewhat pointed front end which helps guide the insertion of fastener 100 into ligament 200 and bone 300. Also, the enlarged diameter of the fastener's shank portion 115 (relative to its shank portion 120) provides added strength to help keep the deployed fastener intact when it is subsequently subjected to stresses in the patient's body. Also, the fastener's ribs 135 are positioned along shank 105 so that they preferably reside inside the bone's interior, softer cancellous region, rather that residing inside the bone's more brittle exterior cortical region. Furthermore, the intersection of the fastener's top end surface 150 and its cylindrical side surface 155 is rounded slightly so as to minimize any interference by the fastener with other bodily parts.

It should also be noted that the features of fastener 100 and the specific manner in which it is intended to be deployed facilitate the use of the fastener in arthroscopic applications wherein the fastener must generally be deployed in a remote location which can be reached only through a narrow cannula providing an access portal of a few millimeters.

It is also to be appreciated that certain changes could be made to the surgical fastener 100 described above without departing from the scope of the present invention.

Thus, for example, the overall appearance of fastener 100 could be maintained but its dimensions changed, e.g. the fastener could be enlarged so that it has a length of 1.420 inches (rather than 0.710 inches as described above), with the various dimensions of the fastener being correspondingly enlarged, or the fastener could be reduced so that it has a length of 0.36 inches (rather than 0.710 inches as describe above), with the various dimensions of the fastener being correspondingly reduced. Alternatively, the dimensions of the fastener could be changed so as to make the fastener longer and thinner, or shorter and fatter, etc. In this regard, it is to be noted that the dimensions of the surgical fastener 100 given above are believed to be optimum for use in attaching ligaments to bones in the shoulder region; however, for other purposes (e.g., for attaching ligaments to bones in the leg region), other dimensions may be more desirable. It is also to be appreciated that as the thickness of fastener 100 is altered, the size of the bore 205, 305 formed in ligament 200 and bone 300 may also need to be correspondingly adjusted so as to enable fastener 100 to properly engage ligament 200 and bone 300 when the fastener is deployed.

It is also anticipated that the thickness of guide wire 400 may also be varied, e.g. guide wire 400 might be increased in diameter to a thickness of approximately 0.06 inches, or guide wire 400 might be reduced in diameter to a thickness of approximately 0.025 inches. Of course, in the event that the thickness of guide wire 400 is changed, the size of the bore 165 in fastener 100 and the size of the internal bores in cannulated drill 500 and hollow driver 600 may also need to be correspondingly changed.

Figure 9:
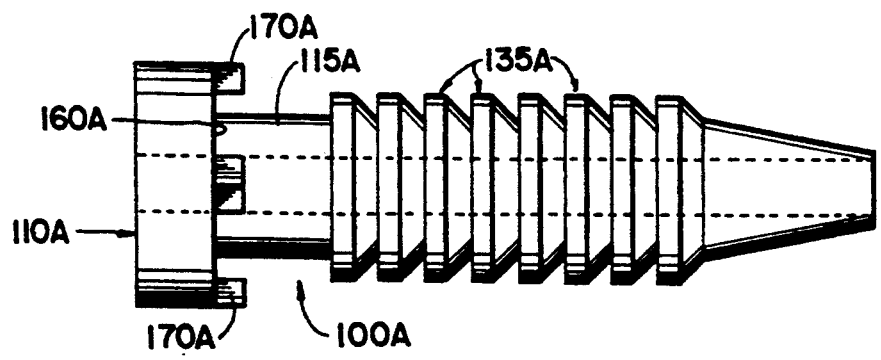
FIG. 9 is a view like that of FIG. 1, except that an alternative form of surgical fastener having eight ribs is shown.
Figure 10:
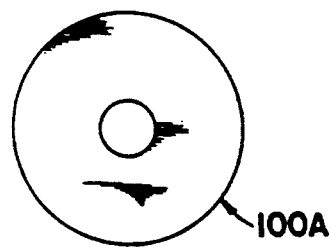
FIG. 10 is a top view of the surgical fastener shown in FIG. 9, taken along line 10—10 of FIG. 9.
Figure 11:
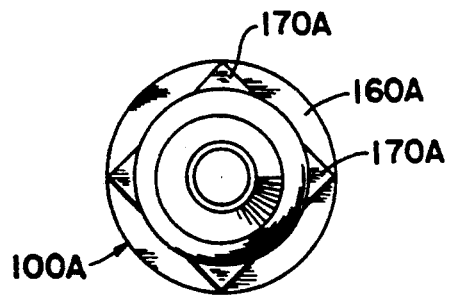
FIG. 11 is a bottom view of the surgical fastener shown in FIG. 9, taken along line 11—11 of FIG. 9.

It is also anticipated that surgical fastener 100 might be formed with more or less ribs 135 than the three ribs shown in FIGS. 1–8. Thus, for example, a surgical fastener 100A having eight ribs 135A is shown in FIGS. 9–11. Also, as seen with fastener 100A of FIGS. 9–11, the ribs may contact one another directly (rather than being spaced from one another as is the case with fastener 100 shown in FIGS. 1–8), and the fastener's shank portion 115A may not be enlarged relative to the remainder of the fastener's shank. Furthermore, it is anticipated that a plurality of ligament-engaging projections 170A could be added to the lower surface 160A of head 110A to enhance the engagement of the fastener's head with ligament 200.

Figure 12:
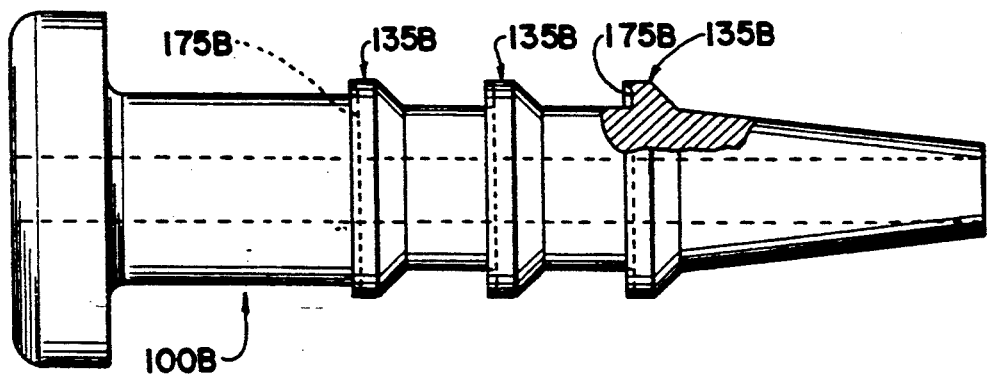
FIG. 12 is a view like that of FIG. 1, except that another alternative form of surgical fastener having a modified rib construction is shown.

It is also anticipated that the fastener's ribs 135 might be undercut slightly at their top sides so as to make them slightly more flexible. Thus, for example, a fastener 100B having undercuts as shown at 175B in each of its ribs 135B is shown in FIG. 12.

It is also to be appreciated that while the foregoing surgical fastener was described in the context of attaching a ligament to a bone, it might also be used to attach other ligament-like objects (e.g. a tendon or some other type of soft tissue), both natural and man-made, to bone, or it might be used to attach ligaments or ligament-like objects to bone-like structures, i.e., the fastener might be used to attach an artificial ligament to a natural bone, or a natural ligament to an artificial prosthesis, etc.

Furthermore, it is also to be appreciated that certain changes might be made in the manner in which the surgical fastener is deployed. Thus, for example, whereas in the foregoing description guide wire 400 is first set and cannulated drill 500 is then coaxially mounted onto the guide wire and then drilled into ligament 200 and bone 300, it is anticipated that the sequence could be altered somewhat so that cannulated drill 500 is first drilled into ligament 200 and bone 300, then while cannulated drill 500 is positioned in ligament 200 and bone 300, guide wire 400 is passed through the cannulated drill's central bore 505 to engage bone 300, and then cannulated drill 500 is withdrawn, leaving guide wire 400 in place in ligament 200 and bone 300. This alternative arrangement may be advantageous in the sense that cannulated drill 500 can act as a supporting cannula to help keep the thin guide wire straight during insertion, although it does have the disadvantage that the guide wire is not present during drilling by cannulated drill 500 so as to act as a guide for the drill.

These and other changes of their type are considered to be within the scope of the present invention.

EXAMPLES

The following examples are provided to illustrate the fabrication of the novel fastener herein disclosed.

EXAMPLE 1

The 3 rib fastener of FIGS. 1–8 was injection molded out of Maxon (R) (a copolymer comprising trimethylene carbonate and glycolide). The fastener had the following dimensions:

| | | |
|---|---|---|
| (1) Rib Diameter | | 0.157 inches |
| (2) Head Diameter | | 0.256 inches |
| (3) Shaft Diameter | - | 0.138 inches |
| (4) Overall Length | | 0.710 inches |
| (5) Center Bore Diameter | | 0.048 inches |

The fasteners were post treated at 110 degrees centigrade for 16 hours, and then ETO (ethylene oxide) sterilized. The fasteners were then implanted in canine humeri and demonstrated to work in a satisfactory manner.

EXAMPLE 2

The 3 rib fastener was molded out of Lactide/Glycolide copolymer (80/20 composition) for the nominal dimensions shown in Example 1 above. The fasteners were tested in canine humeri without any post treatment, and were demonstrated to work in a satisfactory manner.

EXAMPLE 3

The 8 rib fastener of FIGS. 9–11 was molded out of Maxon (see above) and was then coated by dipping in an approximately 10% solution of polylactic acid in methylene chloride. The fasteners were then tested and were found to work in a satisfactory manner.

EXAMPLE 4

Hydroxyapatite powder (Calcitech, San Diego, Calif.) was dry blended with Maxon (see above) and the 3 rib fasteners of FIGS. 1–8 were molded, at an initial loading of 10% hydroxyapatite (HA) by weight. The fasteners were then tested and were found to work in a satisfactory manner.

ADVANTAGES OF THE INVENTION

Numerous advantages are achieved by using the present invention.

First, the present invention provides a novel surgical fastener of the sort adapted to attach soft tissues (e.g. ligaments, tendons and the like) to bone and bone-like structures.

Second, the present invention provides a novel surgical fastener of the sort adapted to attach soft tissues (e.g. ligaments, tendons and the like) to bone and bone-like structures, wherein the fastener is designed to minimize bone necrosis.

Third, the present invention provides a novel surgical fastener of the sort adapted to attach soft tissues (e.g. ligaments, tendons and the like) to bone and bone-like structures, wherein the fastener is designed to be used arthroscopically.

Fourth, the present invention provides novel means for deploying the aforementioned surgical fastener in a remote, e.g. arthroscopic, location.

Fifth, the present invention provides a complete system for attaching soft tissues (e.g., ligaments, tendons and the like) to bone and bone-like structures.

And sixth, the present invention provides a novel method for attaching soft tissues (e.g., ligaments, tendons and the like) to bone and bone-like structures.

What is claimed is:

1. A method for attaching a soft tissue to a bone-like structure, said method comprising the steps of:
   (1) providing a fastener comprising a shank having first and second ends, and a longitudinal axis extending from said first end to said second end, and an enlarged head disposed on said second end of said shank, said shank having at least one rib disposed intermediate its first and second ends, and said fastener having a bore extending completely through said shank and said head along said longitudinal axis;
   (2) positioning said soft tissue against said bone-like structure;
   (3) passing a first end of a guide wire through said soft tissue and into said bone-like structure;
   (4) mounting a cannulated drill having an axial bore therein onto a second end of said guide wire by passing said guide wire through said axial bore, moving said cannulated drill along said guide wire from said second end of said guide wire toward said first end of said guide wire and, using said guide wire as a drill guide, drilling through said soft tissue and into said bone-like structure so as to form a hole therein, and then withdrawing said cannulated drill from said guide wire at said second end of said guide wire;

(5) mounting said fastener coaxially onto said guide wire at said second end of said guide wire by passing said guide wire through said fastener bore;

(6) mounting a hollow driver having an axial bore and a driving surface onto said second end of said guide wire by passing said guide wire through said axial bore, and repeatedly striking said head of said fastener with said driving surface of said hollow driver so as to drive said shank of said fastener through said soft tissue and into said bone-like structure, whereby said head of said fastener will captivate said soft tissue to said bone-like structure;

(7) withdrawing said hollow driver from said guide wire at said second end of said guide wire; and (8) withdrawing said guide wire from said soft tissue and said bone-like structure.

2. A method according to claim 1 including the additional step of sealing said fastener bore with bone wax after the guide wire has been withdrawn from said soft tissue and said bone or bone-like structure.

3. A method according to claim 1 wherein said fastener comprises three ribs.

4. A method according to claim 1 wherein said fastener is formed out of a polymer selected from a group consisting essentially of polypropylene, Hytrel (R) copolyster, homopolymer polyesters, polyethylene terephthalate, polybutylene terephthalate, nylon, polyethylene, polycarbonate, and acrylonitrile butadiene styrene block copolymers, so as to be substantially non-absorbable to the human body.

5. A method according to claim 1 wherein said fastener is formed out of a polymer selected from a group consisting essentially of homo and copolymers of glycolide and trimethylene carbonate, homo and copolymers of lactide and glycolide, and a blend of these homopolymers and copolymers, so as to be substantially absorbable to the human body.

6. A method according to claim 5 wherein said fastener is coated with a polymer selected from a group consisting essentially of caprolactone and glycolide homo and copolymers, and glycolide and lactide homo and copolymers, so as to delay the absorption of the fastener into the human body.

7. A method according to claim 1 wherein said fastener is formed out of a composite comprising a bone growth promoter.

8. A method according to claim 1 wherein said fastener is coated with a functional agent to facilitate delivery of the agent to the implant site.

9. A method according to claim 1 wherein said first end of said shank is substantially pointed.

10. A method according to claim 1 wherein said head comprises at least one projection extending away from said head toward said first end of said shank.

11. A method for attaching a soft tissue to a bone-like structure, said method comprising the steps of:

(1) providing a fastener comprising a shank having first and second ends, and a longitudinal axis extending from said first end to said second end, and an enlarged head disposed on said second end of said shank, said shank having at least one rib disposed intermediate its first and second ends, and said fastener having a bore extending completely through said shank and said head along said longitudinal axis, (2) positioning said soft tissue against said bone-like structure;

(3) drilling through said soft tissue and into said bone-like structure with a cannulated drill having an axial bore therein so as to form a hole through said soft tissue and into said bone-like structure;

(4) while said cannulated drill is in place in said soft tissue and said bone-like structure, passing a first end of a guide wire through said axial bore of said cannulated drill so that said first end of said guide wire engages said bone-like structure;

(5) removing said cannulated drill from said soft tissue and said bone-like structure, while leaving said first end of said guide wire in engagement with said bone-like structure;

(6) mounting said fastener coaxially onto said guide wire at said second end of said guide wire by passing said guide wire through said fastener bore;

(7) mounting a hollow driver having an axial bore and a driving surface onto said second end of said guide wire by passing said guide wire through said axial bore, and repeatedly striking said head of said fastener with said driving surface of said hollow driver so as to drive said shank of said fastener through said soft tissue and into said bone-like structure, whereby said head of said fastener will captivate said soft tissue to said bone-like structure;

(8) withdrawing said hollow driver from said guide wire at said second end of said guide wire; and (9) withdrawing said guide wire from said soft tissue and said bone-like structure.

12. A method according to claim 11 including the additional step of sealing said fastener bore with bone wax after the guide wire-has been withdrawn from said soft tissue and said bone or bone-like structure.

13. A method according to claim 11 wherein said fastener comprises three ribs.

14. A method according to claim 11 wherein said fastener is formed out of a polymer selected from a group consisting essentially of polypropylene, Hytrel (R) copolyster, homopolymer polyesters, polyethylene terephthalate, polybutylene terephthalate, nylon, polyethylene, polycarbonate, and acrylonitrile butadiene styrene block copolymers, so as to be substantially non-absorbable to the human body.

15. A method according to claim 11 wherein said fastener is formed out of a polymer selected from a group consisting essentially of homo and copolymers of glycolide and trimethylene carbonate, homo and copolymers of lactide and glycolide, and a blend of these homopolymers and copolymers, so as to be substantially absorbable to the human body.

16. A method according to claim 15 wherein said fastener is coated with a polymer selected from a group consisting essentially of caprolactone and glycolide homo and copolymers, and glycolide and lactide homo and copolymers, so as to delay the absorption of the fastener into the human body.

17. A method according to claim 11 wherein said fastener is formed out of a composite comprising a bone growth promoter.

18. A method according to claim 11 wherein said fastener is coated with a functional agent to facilitate delivery of the agent to the implant site.

19. A method according to claim 11 wherein said first end of said shank is substantially pointed.

20. A method according to claim 11 wherein said head comprises at least one projection extending away from said head toward said first end of said shank.

21. A method of attaching soft tissue to a bone having an outer hard, cortical region and an inner soft, cancellous region, said method comprising:
providing:
(i) a fastener comprising:
(a) a shank having distal and proximal ends, and a longitudinal axis extending from said distal end to said proximal end,
(b) an enlarged head located at said proximal end of said shank,
(c) at least one rib circumferentially surrounding said shank and said distal and proximal ends of said shank, and
(d) a bore extending longitudinally through said shank and said enlarged head from said distal end to said proximal end,
wherein the longitudinal distance between said enlarged head and said at least one rib is greater than the combined width of the soft tissue and the cortical region of the bone, such that upon engagement of said fastener with the bone, said enlarged head lies against the soft tissue and said at least one rib lies within the cancellous region of the bone, and
(ii) a guide wire adapted to be received in sliding engagement within said bore of said fastener;
forming a hole in the bone adapted to receive said fastener;
coaxially engaging said fastener and said guide wire; and
inserting said fastener through the soft tissue and into the hole in the bone while said fastener is engaged with said guide wire, whereby said enlarged head will hold the soft tissue to the bone.

22. A method of attaching an object to a bone having a relatively hard outer cortical region and a relatively soft inner cancellous region, said method comprising:
providing:
(i) a fastener comprising:
(a) a shank having a distal portion and a proximal portion, and a longitudinal axis extending from said distal portion to said proximal portion,
(b) means for securing an object to said shank, and
(c) at least one rib circumferentially surrounding said shank intermediate said distal and proximal portions of said shank;
forming a hole in the bone, the hole having a diameter smaller than the diameter of said at least one rib; and
installing said fastener in the hole so that said at least one rib engages and bears against the cancellous region of the bone, said fastener being secured to the bone and the object being secured to the bone by said fastener.

* * * * *